United States Patent [19]
Hobbs et al.

[11] Patent Number: 5,249,579
[45] Date of Patent: Oct. 5, 1993

[54] CONTRAST MEDIA INJECTOR

[75] Inventors: Eamonn Hobbs, Queensbury, N.Y.; Irvin F. Hawkins, Gainesville, Fla.; Arthur L. Zimmet, Centerport; John Goodman, Huntington, both of N.Y.

[73] Assignee: E-Z-EM, Inc., Westbury, N.Y.

[21] Appl. No.: 629,180

[22] Filed: Dec. 20, 1990

Related U.S. Application Data

[63] Continuation-in-part of Ser. No. 491,071, Mar. 9, 1990, abandoned.

[51] Int. Cl.$^5$ .................................................. A61B 8/14
[52] U.S. Cl. .............................. 128/662.02; 128/747; 604/23; 604/26
[58] Field of Search ............... 128/655, 662.02, 747; 601/23, 26–28, 49, 67, 30–34

[56] References Cited

U.S. PATENT DOCUMENTS

| | | | |
|---|---|---|---|
| 3,631,847 | 1/1972 | Hobbs | 604/49 |
| 3,812,843 | 5/1974 | Wootten et al. | 128/635 |
| 3,870,072 | 3/1975 | Lindemann | 128/3 |
| 3,880,138 | 4/1975 | Wootten et al. | 128/655 |
| 4,137,913 | 2/1979 | Georgi | 604/67 |
| 4,392,847 | 7/1983 | Whitney et al. | 128/655 |
| 4,611,340 | 9/1986 | Okazaki | 378/95 |
| 4,895,144 | 1/1990 | Cook et al. | 604/30 |

FOREIGN PATENT DOCUMENTS 3802128 3/1989 Fed. Rep. of Germany .

*Primary Examiner*—Stephen C. Pellegrino
*Assistant Examiner*—Michael Rafa
*Attorney, Agent, or Firm*—McAulay Fisher Nissen Goldberg & Kiel

[57] ABSTRACT

An apparatus is provided to deliver carbon dioxide to an animal in a manner which allows the carbon dioxide to totally displace blood in an area of interest and to thus serve as a contrast media for angiographic procedures, or blood displacement media for angioscopic or laser procedures. The apparatus enables the carbon dioxide to flow at varied flow rates, the varied flow rates correlated to the varied flow rate of blood in the animal's vascular system. The flow rate of the carbon dioxide is variable during the course of a single injection.

27 Claims, 4 Drawing Sheets

CONTRAST MEDIA INJECTOR

BACKGROUND OF THE INVENTION

This is a continuation in part of patent application Ser. No. 491,071 filed on Mar. 9, 1990 now abandoned.

The present invention relates to an injector for injecting a gas contrast media into the bloodstream and more particularly to such an injector for injecting carbon dioxide into the bloodstream in a controlled manner.

Carbon dioxide injected into the blood stream can serve as a negative contrast media for angiographic procedures or as a blood displacement media for procedures such as arteriograms, angioscopy and laser therapy.

Liquid iodinated contrast is one presently used contrast media for angiography. The liquid iodinated contrast is injected into the bloodstream at a predetermined flow rate. When liquid iodinated contrast enters the bloodstream, it mixes with the blood and flows downstream. Although iodinated contrast media is generally useful and safe, it can create serious problems and even death in people with iodine allergies.

Saline is a known blood displacement media and is frequently used during laser therapy and angioscopy. Saline has limited use as it cannot be safely injected in large doses. Carbon dioxide, in contrast to saline, has superior light transmittance and thermal insulating properties.

Carbon dioxide, in contrast to known prior art contrast and displacement media, is inexpensive, non-toxic, and is readily released from the body by the normal breathing process. However, there have been problems safely and effectively using carbon dioxide as a contrast media with presently known delivery systems due, in part, to the fact that carbon dioxide is a compressible gas.

When carbon dioxide is injected into the vascular system, it compresses and expands along with the pressure wave created by the cardiac output. Blood forced into the aorta during cardiac systole moves the blood forward in the blood vessels and sets up a pressure wave which travels down the arteries. The arterial pressure rises during systole and lowers during diastole.

The flow rate of blood through the vascular system depends upon the cardiac cycle and blood pressure. The flow rate can be measured directly using known means.

When carbon dioxide is injected into the bloodstream, it forms bubbles. Carbon dioxide does not mix with the blood. For carbon dioxide to function as a viable contrast media or displacement media, it must completely displace the blood in the area of interest. If it does not, any area of blood not displaced will falsely appear to be a stenosis or lesion. The carbon dioxide must completely displace the blood in the area of interest for the entire injection period. For this displacement to occur the carbon dioxide must be injected at a pressure greater than the pressure of the blood itself. However, if the pressure differential between the injected carbon dioxide and the blood is too great a reflux or retrograde flow of carbon dioxide occurs. This reflux necessitates the injection of additional carbon dioxide and further creates safety problems due to the uncontrolled nature of the carbon dioxide flow.

Care must be taken with carbon dioxide to prevent blood clots from forming. Additionally, care must be taken to prevent any pressure spike at the initiation f the carbon dioxide injection. Additionally, care must be taken to avoid an explosive delivery which can cause patient pain. Further, nitrogen and oxygen should be removed from the injector system to insure patient safety and comfort.

It is preferable to inject as little carbon dioxide as possible without sacrificing the integrity of the procedure and, it is preferable to have the carbon dioxide injected at the lowest pressure which still permits complete displacement of blood.

Accordingly, it is an object of the present invention to provide a device for introducing carbon dioxide into the bloodstream such that carbon dioxide can function as a contrast and blood displacement medium.

It is another object of the present invention to provide such a device which enables the carbon dioxide to completely displace the blood in the area of interest for the entire injection.

It is yet another object of the present invention to provide such a device which minimizes safety hazards and enhances patient comfort.

Yet a further object of the present invention is to provide such a device which minimizes problems, such as blood clots or explosive delivery.

BRIEF DESCRIPTION

In one embodiment of the present invention an apparatus is provided to inject gas, in a controlled manner, into an animal's vascular system. The apparatus has an inlet port and an outlet port for permitting gas to enter and to exit from the apparatus. The apparatus includes a mechanism for controlling the flow rate at which the gas is delivered so that the flow rate of the gas correlates to the flow rate of blood in the animal's vascular system. The mechanism for controlling the flow rate enables the flow rate to be varied during the course of an injection.

DETAILED DESCRIPTION OF THE PREFERRED EMBODIMENT

Figure 1:
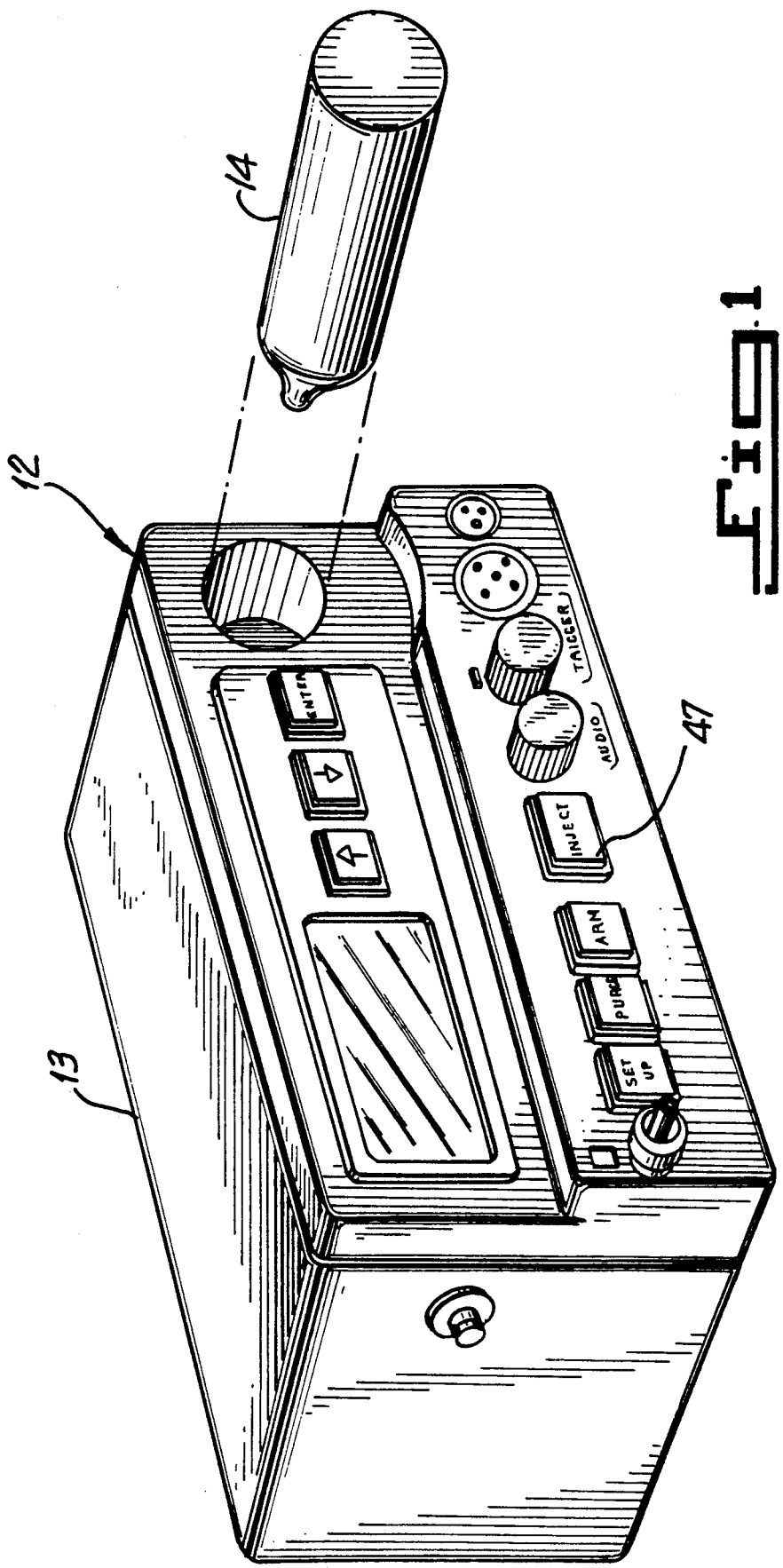
FIG. 1 is an exploded perspective view of a portion of the apparatus of the present invention showing the injector prior to the carbon dioxide source being connected thereto.
Figure 2:
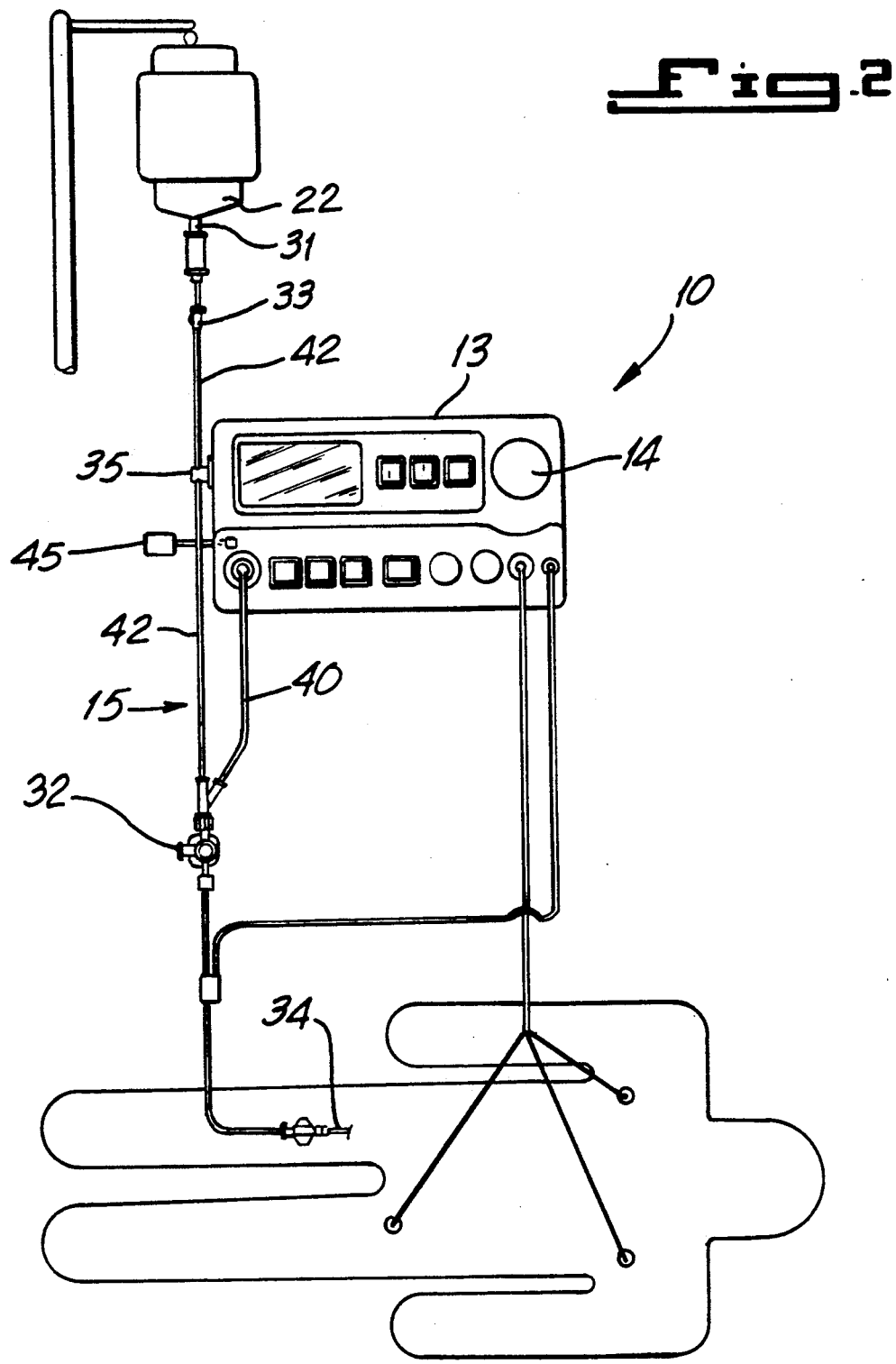
FIG. 2 is a schematic view showing the apparatus of the present invention.
Figure 3:
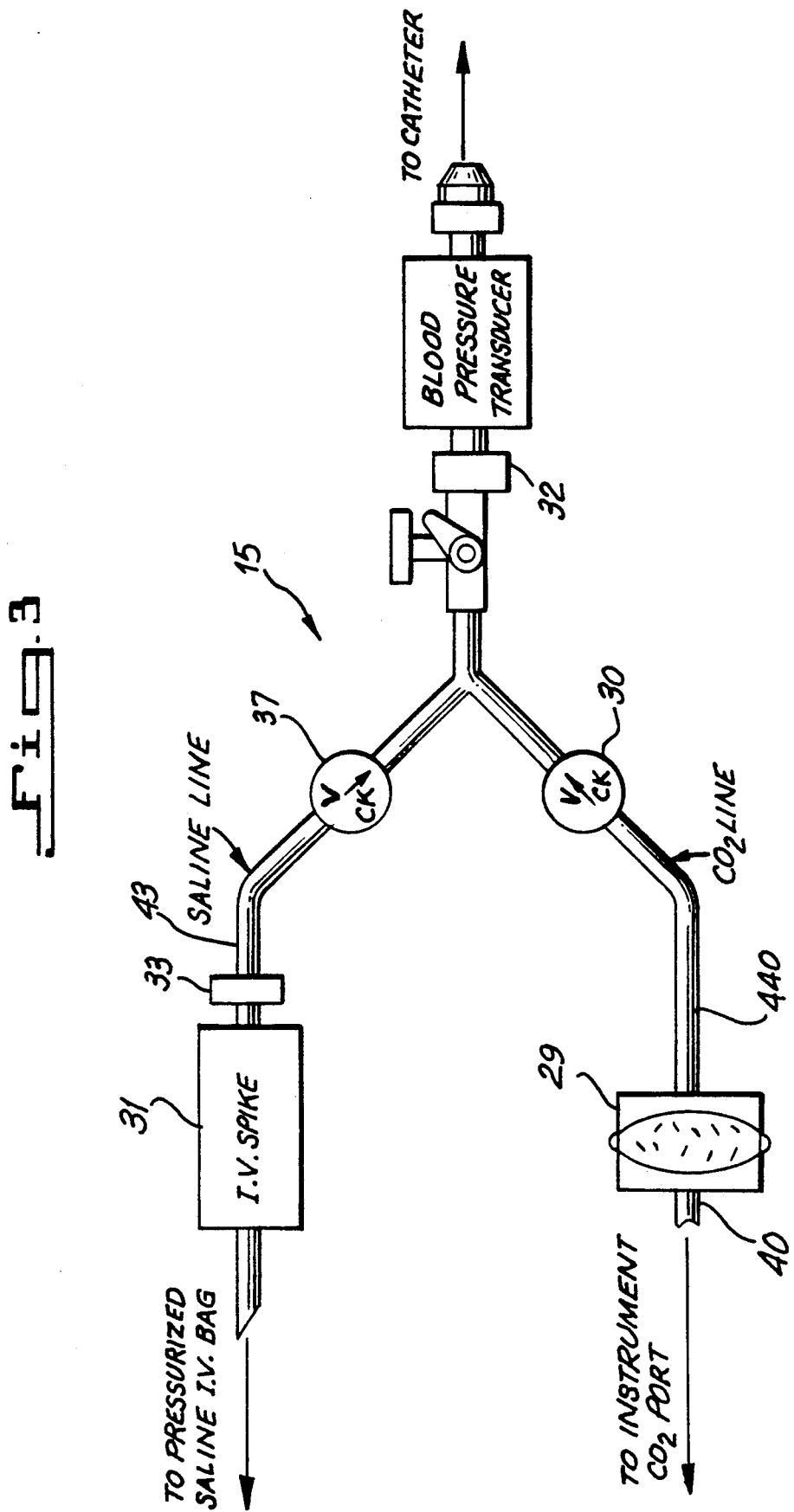
FIG. 3 is a schematic view showing the sterile system of the apparatus of the present invention.
Figure 4:
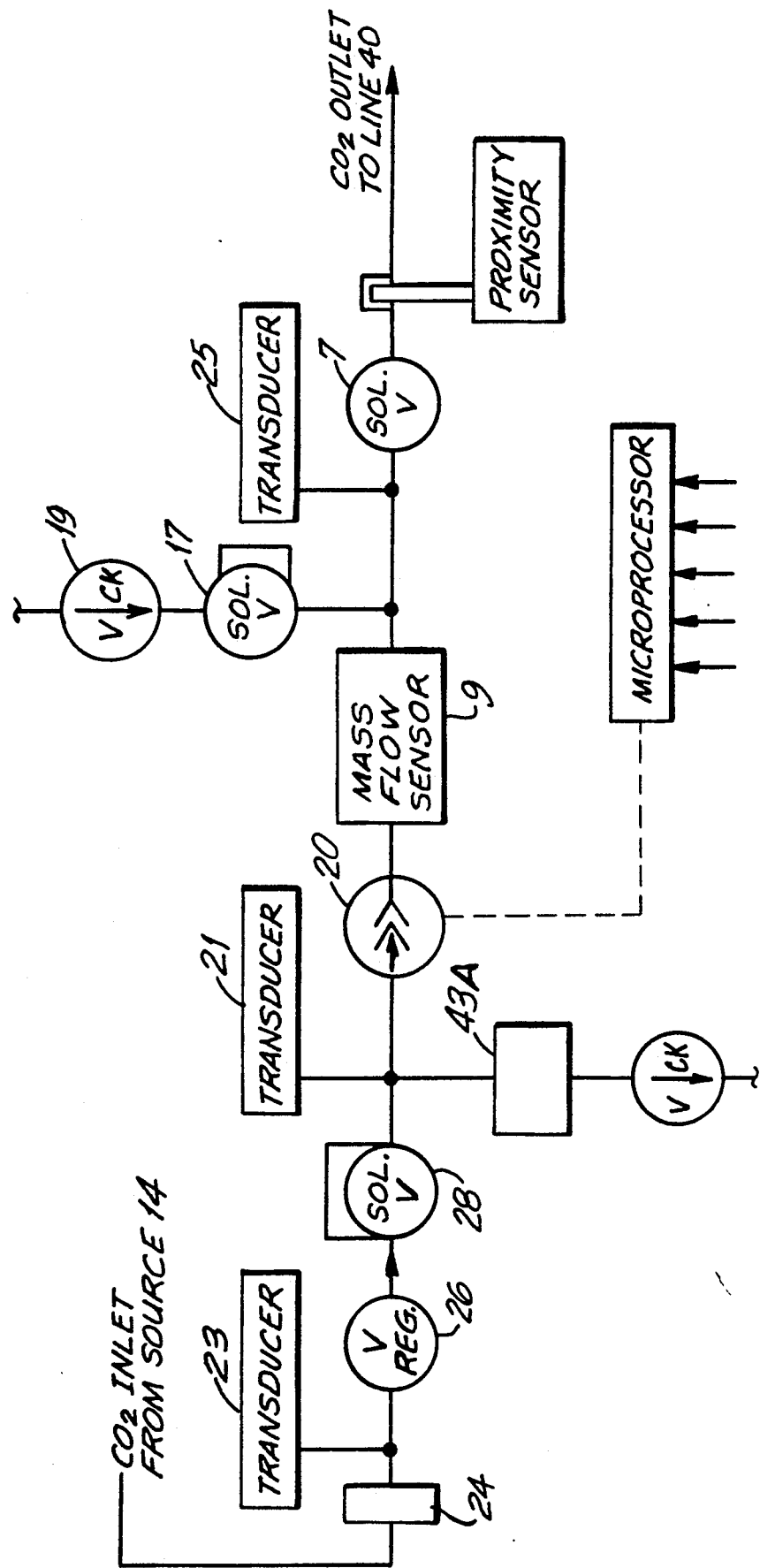
FIG. 4 is a schematic view of a portion of the injector of the present invention to indicate the path of flow of carbon dioxide therethrough.

Referring now to the drawings, the reference numeral 10 generally denotes the apparatus of the present invention. Apparatus 10 is capable of delivering carbon dioxide, or any other appropriate gas, to a person's bloodstream in a controlled, variable manner which synchronizes the flow of the injected carbon dioxide to the pulsatile flow of the blood in the area to be studied.

Apparatus 10 uses carbon dioxide from a carbon dioxide source 14. In a preferred embodiment of the invention, source 14 is a disposable TA4 cylinder which contains a predetermined volume of carbon dioxide.

Carbon dioxide flows from source 14 through an injector 13, through a sterile segment 15 and is then introduced into a patient's blood stream via a catheter 34. The flow rate of the carbon dioxide is controlled by a valve 20, in injector 13, which has a variable orifice. Valve 20 is in turn controlled by a microprocessor 12. In a preferred embodiment of the invention valve 20 is a DC controlled valve which is capable of regulating gas flow rates between 3 cc/sec to 225 cc/sec. In use the valve is regulated to a first higher flow rate during systole and a second lower flow rate during diastole. The response time of the valve orifice in switching between the systolic and diastolic flow rates is about 3 milliseconds.

Other means to control flow may be used instead of a variable orifice valve. Examples of such means is the use of a two intermediate reservoir system which holds the carbon dioxide at two different pressures, a series of cascading valves coupled to calibrated orifices, and two variable pressure regulators.

The orifice of valve 20 is controlled by a microprocessor 12 to achieve the desired pulsatile flow rate of carbon dioxide. To do this the following input data is provided to microprocessor 12. The operator makes a clinical determination of the desired flow rate to be delivered during systole and inputs this, into microprocessor 12. The flow rate of carbon dioxide during diastole is a predetermined percentage of the systolic flow rate and in the preferred embodiment of this invention is about twenty percent of the systolic flow rate. An operator inputs into microprocessor 1 a clinically determined volume of carbon dioxide that is to be injected during the injection procedure and also provides the microprocessor with the length and the diameter of catheter 34. Information concerning the patient's cardiac cycle and blood pressure is provided to the microprocessor using conventional means. In the preferred embodiment of the invention blood pressure information is provided by a disposable blood pressure transducer mounted in sterile system 15 and cardiac cycle information is provided by coupling apparatus 10 to a standard 3-lead electrocardiogram. From this input data the microprocessor determines, based on known calibration algorithms, the amplitude and duration of the opening of the valve 20 orifice. The microprocessor 12 synchronizes the opening and closing of the valve 20 orifice to the systolic and diastolic portions of the patient's cardiac cycle so that the flow of carbon dioxide is in turn synchronized to the patient's blood pressure wave.

When carbon dioxide is not being injected into a patient, a saline drip is injected to prevent clotting of blood in the catheter. Both the carbon dioxide and the saline flow through the common sterile segment 15. The carbon dioxide flows through the sterile segment 15 after it has gone through injector 13. The sterile segment 15 thus couples both a saline source and injector 13 to catheter 34 and does's using two lengths of sterile tubing 40, 42 joined at their distal ends into a single three-way stopcock 32.

The path of flow of saline is as follows. Pressurized saline from a bag 22 or other source is connected to sterile segment 15 using spike 31. A roller clamp 33 and an external pinch valve 35 are provided to control the flow of saline through tubing 42. The saline flows through a check valve 37 which prevents reflux of carbon dioxide into the saline bag 22, then through a blood pressure transducer 39 and then through high pressure three-way stopcock 32 into catheter 34. External pinch valve 35 insures that saline and carbon dioxide do not simultaneously flow into the catheter and also insures that saline flows into the catheter whenever carbon dioxide does not so flow.

The path of flow of the carbon dioxide is as follows. After leaving source 14 the carbon dioxide flows into injector 13. In injector 13 the carbon dioxide flows past a two micron filter 24 which removes gross particulate contaminate from the carbon dioxide. It next flows through a pressure regulator 26 which lowers the pressure as fed from source 14 and standardizes the pressure of the carbon dioxide in the injector. After that the carbon dioxide flows through an on/off valve 28 which is capable of halting the flow of the carbon dioxide in injector 13. The carbon dioxide then flows through valve 20. After flowing through valve 20, the carbon dioxide flows through a mass flow sensor 9 which feeds instantaneous flow rate data to microprocessor 12. The carbon dioxide then flows through on/off valve 7 immediately proximal to the point of connection of the sterile segment to injector 13. Then the carbon dioxide exits injector 13 and flows into sterile segment 15 through tubing 40 where it flows through a sterilizing filter 29, a check valve 30, a blood pressure transducer 39 and stopcock 32 into the patient via catheter 34. All of the valves and filters in the sterile segment 15 are hermetically sealed and bonded.

In use, catheter 34 is introduced into a patient, and then the sterile segment 15 is connected to the catheter. The stopcock 32 is put in a back flow position to evacuate air from the catheter 34.

Prior to commencing an injection of carbon dioxide and after the connection of the catheter to the closed system, apparatus 10 is purged. The purge removes ambient air, which contains a high percentage of nitrogen, from the apparatus to insure patient safety. During this purge the carbon dioxide is allowed to run through injector 13 and sterile segment 15 with stopcock 32 in its open position to vent the air in the system to the atmosphere. After a sufficient volume of carbon dioxide is run through the injector, the stopcock 32 is placed in its injecting position. A purge cycle must be run anytime the sterile segment has been disconnected from the injector 13 and anytime a new source 14 is connected to injector 13.

At the beginning of each injection a predetermined volume of carbon dioxide is dispensed into the sterile segment. The volume of carbon dioxide injected is just enough to clear the saline from the sterile segment and catheter. The purpose of this is to establish a continuous column of carbon dioxide between the source and the patient. Because of its gaseous nature the carbon dioxide compresses when exposed to pressure. This presents a problem when an injection commences. Without this flushing injection of carbon dioxide, the gas would compress further as it pushed the column of saline. This compression would be relieved in the form of a transient explosion as the carbon dioxide reached the end of the catheter. To prevent this, a continuous column of carbon dioxide between injector 13, the sterile segment 15 and the patient's blood stream is created prior to injection. This continuous volume of carbon dioxide is generated by flushing out the saline in the system using the small volume injection of carbon dioxide to push the saline out in front of it. Too much carbon dioxide, at this point, would cause explosive decompression and blood vessel damage.

As soon as adequate time has elapsed to allow the predetermined volume of carbon dioxide to expand through the sterile segment and catheter, injection at the predetermined systolic and diastolic flow rate is commenced. Injection commences upon the detection of an R-wave peak. And, as heretofore set forth, the orifice of valve 20, under the control of microprocessor 12, will open and close synchronous to the systolic and diastolic portions of the patient's cardiac cycle to thus vary the pulse flow rate of the carbon dioxide into the patient so as to enable total displacement of blood in the area of interest. The systolic segment time and diastolic segment time are determined by the blood pressure transducer 39 using known relationships. Injection will proceed until the amount of carbon dioxide previously determined by the operator has been delivered. This injection will generally extend through a plurality of cardiac cycles.

At the completion of an injection, residual compressed carbon dioxide is vented to the atmosphere through a solenoid valve 17. The venting of this residual gas prevents additional carbon dioxide from being accidentally injected into the patient. Valve 17 remains open until a pressure transducer 25 senses that the residual pressure in the injector is nominally above physiologic pressure.

Apparatus 10 includes a number of mechanisms for enhancing the safety of the injection procedure. Additional safety is provided by pressure transducer 23 which measures the pressure in source 14. This pressure information is used to determine if source 14 contains an adequate amount of carbon dioxide for the injection and to determine if the source 14 is connected to the injector 13. If there is not sufficient carbon dioxide for an injection the microprocessor will not allow an injection to commence. If the source 14 has been disconnected the microprocessor will give an appropriate signal to alert the operator that a purge of the system must be run prior to an injection.

For additional safety, mass flow sensor 9 is used to determine instantaneous flow rate through injector 13 and to determine the total amount of carbon dioxide delivered during a injection. If the instantaneous flow rate is not within input parameters or if the predetermined volume has been delivered microprocessor 12 will halt the injection. An additional safety mechanism is provided by having microprocessor 12 calculate the expected duration of an injection and having the microprocessor time the actual injection. Again, microprocessor 12 will terminate injection where the desired volume has not been delivered in the expected time.

Signals from pressure transducer 21 are also used to monitor the functioning of pressure regulator 26 and to give an appropriate message if the pressure regulator 26 is not working correctly.

A gas sensor 43 may be placed in injector 13 to sample the carbon dioxide for possible contamination. In a preferred embodiment, gas sensor 43 is a fast acting oxygen sensor with sensitivity in the ppm range. The exhausted gas from sensor 43 is vented to atmosphere through a one-way check valve to ensure no entrainment of room air into the carbon dioxide gas stream.

Proximity sensor 45 is used to detect if sterile segment 15 is connected to injector 13. This information is used by microprocessor 12 to determine if a purge cycle needs to be run.

Panel 47 is used to input data into microprocessor 12 and is further used to display information to the operator.

Catheter 34 is disposable and catheters of different lengths and diameter are contemplated for use in apparatus 10, the length and diameter of the catheter being selected by the operator based upon varied criteria including the vessel into which the carbon dioxide will be injected.

Sterile segment 15 is disposable and it is contemplated that a new sterile segment will be used for each patient.

Apparatus 10 provides a safe and efficient way to deliver a pulsatile flow of carbon dioxide to a patient and to enable the carbon dioxide to serve as a contrast media.

Blood Pressure Transducer 39 is monitored to ensure that the sterile segment 15 is not connected to a patient prior to allowing a purge to commence. This monitoring is done by determining if a blood pressure wave form can be detected. The detection of such a wave form indicates that stopcock 32 is not in the correct position for the purge sequence.

For safety the pressure in source 14 should be constant. This pressure is monitored using transducer 23. If there is a drop in this pressure after a purge cycle, another purge cycle is required prior to commencing an injection.

The actual flow rate delivered by injection 13 is a function of gas pressure on the upstream side of valve 20, control current provided to valve 20 and the size and length of the catheter 34. To insure flow rate accuracy the upstream gas pressure should be at a stable pre-set valve and this pressure is monitored using pressure transducer 21.

R-wave internal is measured by microprocessor 12 to ensure that it is within physiologically normal ranges. Additionally, R-wave interval is monitored during an injection to ensure that there is continuity of R-waves during the injection. The purpose of these monitoring functions is to ensure that clinically efficacious studies are generated from each injection and that the patient is not exposed to more carbon dioxide than necessary.

Microprocessor 12 has a delay program to prevent sequential injections from occurring within a five minute time span. This to ensure that the carbon dioxide delivered during an injection is fully absorbed by the body prior to a subsequent injection. This minimizes the risk of ischemia.

Microprocessor 12 is programmed to limit injection volume to 1000 cc to prevent excessive injection volumes from being administered which could result in carbon dioxide build-up resulting is ischemia.

What is claimed:

1. Apparatus for delivering gas into an animal's cardio-vascular system to enable the gas to function as an angiographic contrast medium comprising:
    a source of the desired gas,
    a catheter adapted to be coupled into the animal's cardio-vascular system,
    injection control means responsive to the cardiac cycle to provide a first control signal during systole and a second control signal during diastole,
    valve means connecting said source to said catheter, said valve means being responsive to said control signals to provide said gas at a first rate during systole and a second rate during diastole.

2. The apparatus of claim 1 wherein said rate during diastole is a predetermined percentage of said rate during systole.

3. The apparatus of claim 1 further comprising:
    volume measuring means to provide a signal to indicate the cumulative volume of gas being injected during an injection procedure, and shut off means responsive to said volume indicator signal to shut said valve when said volume has reached a predetermined value.

4. An apparatus for injecting gas into an animal in a manner which allows the gas to totally displace blood in an area of interest, the apparatus comprising:
an injector comprising means for connecting to a source of gas;
a catheter comprising means for connecting to said injector and through which the gas enters into the animal;
said injector comprising means for varying the flow rate of gas through the injector and the catheter at a first flow rate during systole and a second flow rate during diastole so that a pulsatile flow of gas synchronous to the flow of blood in the animal's vascular system is achieved.

5. The apparatus of claim 4 and further comprising means to regulate the pressure of the gas in the apparatus.

6. The apparatus of claim 4 and further comprising means to vent gas from the apparatus.

7. The apparatus of claim 4 and further comprising a plurality of pressure transducers to sense the pressure of the gas at various points in the apparatus to monitor proper functioning of the apparatus for patient safety.

8. The apparatus of claim 4 and further comprising a mass flow sensor to provide the microprocessor with information to determine if the flow rate of gas and amount of gas being delivered is within the input parameters so that the microprocessor can terminate injection where flow rate or volume are not within input parameters.

9. The apparatus of claim 4 wherein said gas is carbon dioxide.

10. The apparatus of claim 9 and further comprising a sterile segment including means for connecting to said injector and said catheter, said sterile segment, for transporting carbon dioxide or saline solution to the catheter, the saline solution preventing clotting of blood in the catheter.

11. The apparatus of claim 9 and further comprising means to sense the presence of contaminants within the apparatus.

12. The apparatus of claim 9 wherein said sensing means senses the presence of oxygen.

13. The apparatus of claim 4 wherein said means flow rate varying includes a valve having a variable orifice and a microprocessor for controlling the orifice size of the valve using selected input data.

14. The apparatus of claim 13 wherein said selected input data includes the length and diameter of the catheter, a first flow rate, the volume of carbon dioxide to be delivered, blood pressure information from the animal and information concerning the animal's cardiac cycle.

15. The apparatus of claim 14 and further comprising a plurality of pressure transducers to sense the pressure of the carbon dioxide at various points in the apparatus to monitor proper functioning of the apparatus for patient safety.

16. The apparatus of claim 15 and further comprising a timer.

17. The apparatus of claim 16 wherein said microprocessor comprises means for calculating an expected injection time and comparing it to actual injection time to terminate injection when actual time exceeds expected time.

18. A method of delivering gas into an animal's vascular system to enable the gas to function as an angiographic contrast medium, the method including the steps of:
(a) determining a desired flow rate of gas to be delivered during systole;
(b) determining a desired flow rate of gas to be delivered during diastole;
(c) determining the total volume of gas to be delivered;
(d) introducing the gas into the animal using a catheter;
(e) gathering, on an on-going basis, information relating to the animal's cardiac cycle;
(f) gathering information relating to the animal's blood pressure;
(g) providing a microprocessor with the information determined in steps (a), (b), (c), (e) and (f) and with the length and diameter of the catheter;
(h) providing an injecting apparatus and connecting said apparatus to both said catheter and to a source of gas, the injecting apparatus including means to vary the flow rate of gas through the apparatus, said means being controlled by said microprocessor such that the gas will flow at a first flow rate during systole and at a second flow rate during diastole to totally displace the blood in an area of interest to enable angiographic study.

19. The method of claim 18 wherein said gas is carbon dioxide.

20. The method of claim 19 and further including the step of providing a saline drip to enter the catheter when not injecting carbon dioxide to prevent the clotting of blood.

21. The method of claim 19 and further including the step of purging ambient air from the injecting apparatus.

22. The method of claim 19 and further including the step of establishing a continuous column of carbon dioxide between the injecting apparatus and the animal by injecting a predetermined volume of carbon dioxide through the apparatus.

23. A method of delivering gas into an animal's cardiovascular system to enable the gas to function as an angiographic contrast medium comprising the steps of:
injecting the gas at a first predetermined flow rate during systole an a second predetermined flow rate during diastole which synchronizes with systolic and diastolic phases of the cardiac cycle to provide total displacement of blood by the gas in an area of interest.

24. The method of claim 23 wherein said rate during diastole is a predetermined percentage of said rate during systole.

25. The method of claim 24 wherein said predetermined percentage is about twenty percent.

26. The method of claim 23 wherein said step of injecting is undertaken over a plurality of cycles of systole and diastole.

27. The method of claim 23 wherein said step of injecting is undertaken over a plurality of cycles of systole and diastole.

* * * * *